US008734359B2

(12) United States Patent  (10) Patent No.: US 8,734,359 B2
Ibanez et al.  (45) Date of Patent: May 27, 2014

(54) METHOD AND SYSTEM FOR DETERMINING AN INDIVIDUAL'S STATE OF ATTENTION

(75) Inventors: Noelia Rodriguez Ibanez, Barcelona (ES); Mireya Fernandez Chimeno, Barcelona (ES); Juan Jose Ramos Castro, Barcelona (ES); Miguel Angel Garcia Gonzalez, Barcelona (ES); Eduard Montseny Masip, Barcelona (ES); Daniel Bande Matinez, Barcelona (ES)

(73) Assignee: Fico Mirros, S.A., Barcelona (ES)

( * ) Notice: Subject to any disclaimer, the term of this patent is extended or adjusted under 35 U.S.C. 154(b) by 555 days.

(21) Appl. No.: 12/849,267

(22) Filed: Aug. 3, 2010

(65) Prior Publication Data

US 2011/0028857 A1  Feb. 3, 2011

(30) Foreign Application Priority Data

Aug. 3, 2009  (EP) ..................... 09382133

(51) Int. Cl.
  *A61B 5/08*  (2006.01)
(52) U.S. Cl.
  USPC ........................................ 600/529
(58) Field of Classification Search
  USPC .................. 600/529–543; 340/575
  See application file for complete search history.

(56) References Cited

U.S. PATENT DOCUMENTS 5,689,241 A  11/1997  Clarke, Sr. et al.
6,070,098 A *  5/2000  Moore-Ede et al. .......... 600/544
7,304,580 B2  12/2007  Sullivan et al.
7,578,793 B2 *  8/2009  Todros et al. ............... 600/484
2005/0190062 A1  9/2005  Sullivan et al.
2005/0256420 A1  11/2005  Norman et al.
2005/0273264 A1  12/2005  Gern et al.
2006/0132295 A1  6/2006  Gern et al.

FOREIGN PATENT DOCUMENTS

DE  4400207 A1  7/1994
EP  1095617 A1  5/2001
WO  WO-03057025 A2  7/2003
WO  WO-2006131257 A1  12/2006

OTHER PUBLICATIONS

Imhoff M. et al, "Smart Alarms from Medical Devices in the OR and ICU", Baillier's Best Practice and Research, Clinical Anesthesiology, 2009, V. 23, No. 1,1, 1521-6896.

* cited by examiner

*Primary Examiner* — Navin Natnithithadha
(74) *Attorney, Agent, or Firm* — Blue Filament Law PLLC; Avery N. Goldstein (57) ABSTRACT

The present invention relates to a method and a system designed to determine an individual's state of attention from an individual's respiratory signal. The method of the invention comprises a first learning step, wherein the characteristics of an individual's normal state are determined by selecting a respiratory signal fragment that is considered to be normal according to a pre-established criterion, and a second analysis phase, wherein the individual's state of attention is determined from parameters extracted from the respiratory signal on the basis of some pre-defined rules and the individual's normal state previously characterised. The method of the invention is implemented in two embodiments. A first embodiment is based on the identification of pre-defined patterns in the respiratory signal and, in the second embodiment, an index indicative of the variability of the respiratory signal is defined.

28 Claims, 7 Drawing Sheets

METHOD AND SYSTEM FOR DETERMINING AN INDIVIDUAL'S STATE OF ATTENTION

RELATED APPLICATIONS

This application claims priority benefit to European Application No. EP09382133.8 filed Aug. 3, 2009; the contents of which are hereby incorporated by reference.

TECHNICAL FIELD OF THE INVENTION

This invention belongs to the field of systems designed to monitor an individual's state of attention, detect an undesirable state and possibly enable the activation of an alert.

DESCRIPTION OF THE RELATED STATE OF THE ART

In tasks such as driving a vehicle or handling machinery, and those that involve supervision or surveillance designed to detect a potential risk situation, it is essential to keep a high degree of attention. It must be taken into consideration that occasionally these tasks are monotonous or require little active participation on the part of the subject performing them, which, in turn, contributes to reducing the subject's level of attention. In such tasks, the subjects performing them take responsibility for their own safety and that of other people; therefore, a temporary lack of attention, associated, for example, with a distraction, a state of fatigue or a sleep episode, is a frequent cause of errors and slips which may degenerate into a risk to themselves or to others.

The above-mentioned tasks require a number of skills that are significantly reduced when there is a lack of attention. In the case of drowsiness, for example, numerous studies on sleep deprivation show that, at 18 hours of deprivation, there is an increase in the reaction time and hypersensitivity to distractions (difficulty in keeping attention, specially in continuous, routine tasks). If the deprivation continues for a longer period of time, symptoms of confusion, difficulty in expressing oneself, etc., appear.

The effects of sleep loss are cumulative and more evident in the execution of monotonous tasks, such as some of the above-mentioned activities. Occasionally, the mechanisms used to cope with this sleep deficit may make the subjects unaware of the accumulated loss of sleep, which makes them particularly vulnerable to episodes of sudden drowsiness, primarily in situations where attention is greatly reduced (for example, during a long period of immobility due to the posture in executing said task), and an irresistible drowsiness and even brief sleep episodes may occur.

In the case of automobile driving, in 2008 drowsiness was the cause of 30% of traffic accidents, according to the Spanish Traffic Agency. This percentage is even greater if we take into consideration that only those individuals who survived these accidents may be counted in the statistics, and that approximately 11 million adult drivers admit to having had an accident or having been close to having an accident because they fell asleep or were too tired to drive.

Similarly, a state of fatigue severely affects mental capacities, increases the reaction time, makes the assimilation of information difficult, hinders social skills and reduces the ability to reason in a logical manner. There are studies which consider that serious human and ecological catastrophes that were the result of nuclear leaks and toxic product spills were related to human errors caused or aggravated by the state of fatigue of the individuals involved.

Various methods and devices are known, aimed for the most part at detecting drowsiness in vehicle drivers. Most of these methods and devices are based on the subject's way of driving and extract information about use of the steering-wheel, lane departures, and zig-zagging. The most common system is that composed of a lane departure detector combined with other sensors, which measure data such as the distance to the vehicle in front, speed, or use of the clutch.

Document US2006132295A discloses a driver-aid system that detects the edge of a lane and/or the lane marks in order to warn the driver of a risk of lane departure. Document US2005273264A discloses a method and a device designed to warn a driver of lane departure, wherein a first analyser detects lane departure on the basis of image acquisition, vehicle data and/or the driver's activity, and a second analyser evaluates the driving situation. Document WO06131257A discloses a method and a device designed to recognise when the driver of a vehicle is distracted by detecting an inactivity phase in the use of the steering-wheel followed by a turning action that exceeds a certain threshold.

These systems have the disadvantage that they are not capable of distinguishing whether a certain way of driving corresponds to an anomalous state in the subject or, on the contrary, it is due to certain road features, traffic conditions or even that subject's normal driving mode. Consequently, there may be problems related to false positives caused by poor road conditions, road works, poorly painted road lines, weather, rain and certain driving styles, amongst other factors.

Some documents combine driving analysis systems with the capture of biomedical signals, generally related to the heart rate or blood pressure. Document DE4400207A1 discloses a device and a method designed to warn about drowsiness while driving. The method uses pulse rate and vehicle direction measurements, which are compared to reference values in order to detect the degree of wakefulness. Furthermore, different alarms are specified which are progressively activated as a function of the driver's degree of wakefulness.

Document U.S. Pat. No. 7,304,580B2 discloses a medical surveillance system which, in one embodiment, can be adapted for use as a monitoring system for vehicle drivers. A series of sensors collect information about the drivers, the data are analysed and, when the measured data exceed a threshold value, drivers can be warned that they are close to a state of drowsiness or another potentially dangerous physical state. The sensors measure the heart rate, the respiratory rate and the driver's movements, among other data.

Finally, other systems and methods are based on the capture of driver gestures, such as blinking, pupil dilation, eye movement, or head movement. Document U.S. Pat. No. 5,689,241 discloses a device designed to detect drowsiness in drivers that captures images of the driver's eyes in order to detect lack of movement, and combines it with temperature measurements in the nose and mouth area, which are also representative of the driver's condition. Drivers' normal profiles are immediately determined following ignition, and the range of colours of the drivers' open eyes as well as their exhalation temperatures in an alert state are calculated.

These systems and methods exhibit a number of operational problems when light conditions are not suitable; also, they are affected by the driver's movements and those based on the detection of eye images do not operate correctly when the driver wears eyeglasses.

Consequently, there is a need for a method that makes it possible to determine an individual's state of attention in a robust, reliable manner, without the limitations of the existing methods, and which avoids the effect of variability between individuals on the common methods based on the analysis of biomedical data.

SUMMARY OF THE INVENTION

The disadvantages present in existing systems and methods are removed by the method for determining an individual's state of attention according to claim 1, the system designed to determine an individual's state of attention according to claim 23 and the computer programme according to claim 28. The dependent claims define preferred embodiments of this invention.

Within the context of this invention, state of attention will be understood to mean the capacity to persistently focus on a specific stimulus or activity. An abnormal state of attention will be understood to mean any state that entails easy distractability and/or difficulty in performing tasks or concentrating in work. The following table shows examples of states considered to be normal and states considered to be abnormal or undesirable in different applications.

| Normal states of attention | Anomalous or undesirable states of attention |
|---|---|
| wakefulness consciousness soberness, serenity | fatigue, drowsiness unconsciousness drunkenness, under the effect of alcohol and/or drugs |

Stress, nervousness, worry and similar states will also be considered to be anomalous states of attention.

One feature of this invention is that it provides a method for determining an individual's state of attention on the basis of a respiratory signal.

The method of the invention operates in two steps. In the first step, the individual's normal respiratory characteristics are learnt. In the second, an analysis of the respiratory signal is performed in order to identify the individual's state of attention on the basis of certain pre-defined rules and the individual's normal state as characterised.

During the learning step, a fragment wherein the respiratory signal has suitable characteristics to be considered as normal for that individual is located on the basis of the characteristics of the respiratory signal. Whether or not a respiratory signal fragment can be considered to be normal is determined on the basis of a given criterion, and the following criteria, amongst others, are possible:
  determining the variability of the respiratory signal in the signal fragment considered, or
  evaluating the degree of similarity of the respiratory signal fragment considered with respect to a model respiratory signal pattern, or
  evaluating the homogeneity of certain given variables, preferably amplitude and/or frequency, in the respiratory cycles comprised within the respiratory signal fragment considered.

Once the fragment of the respiratory signal considered to be normal has been selected, certain representative characteristics of the individual's normal state are stored, such that the method may be suited to that specific individual. In order to characterise the individual's normal state, at least one parameter extracted from the respiratory signal and/or a respiratory signal pattern, wherein the shape of the signal is also considered, can be stored.

The normal respiratory fragment can be sought within a given time interval or at any time during the process of determining the individual's state of attention, and it is possible to update the state characterised as normal if a second fragment selected from the respiratory signal meets the pre-established criterion better than a first, previously selected respiratory signal fragment. In the event that no respiratory signal fragment is found which meets said pre-established criterion, the method of the invention specifies that the individual's normal state can be characterised on the basis of data stored in a memory device, for example, previously stored data about the same individual or data from a plurality of subjects that statistically represent a population.

In the method of the invention, the respiratory signal is segmented and at least one parameter of the respiratory signal is extracted from each segment in order to determine the individual's state on the basis of certain pre-defined rules and the individual's state characterised as normal. Within the context of the invention, a segment of the respiratory signal is taken to mean one cycle of the respiratory signal, understood as inhalation and exhalation, a multiple of a cycle or a sub-multiple of a cycle.

The method of the invention has the advantage of selecting in an intelligent way in any part of the respiratory signal record a respiratory signal fragment that can be considered as normal if it fulfils a pre-established criterion.

In an embodiment of the method of this invention, following the determination of the individual's state of attention, the individual may be informed about the result of said determination. The process of informing the individual may be performed continuously or only in the event that a given requirement is met, for example, if the state determined is not the state characterised as normal or if the state determined has been pre-defined as an anomalous state or a state that entails a potential risk. In this case, an alarm may be activated, for example, a visual, acoustic, or haptic alarm, in order to warn the individual about an undesirable state of attention.

Additionally or alternatively, the method of this invention may comprise notifying the result of the determination of the individual's state of attention to an alert reception centre.

The method of the invention is applicable to situations where monitoring an individual's state of attention is necessary and/or desirable: for example, if the individual is a vehicle driver, a machinery operator, or a control panel supervisor.

The method for determining an individual's state of attention has the advantage of making it possible to supplement the determination of the state of attention obtained from the respiratory signal with data or measurements from a different source, such as other physiological measurements, data about the individual's behaviour, or parameters obtained from the CAN BUS, if a vehicle is involved.

In a first embodiment, the method for determining an individual's state of attention comprises obtaining at least one fuzzy parameter from the at least one parameter extracted from each segment. In this embodiment, the determination of the individual's state comprises evaluating the degree of similarity of each segment of the respiratory signal with a plurality of pre-determined respiratory patterns, by comparing the at least one fuzzy parameter of each segment with characteristic parameters of said pre-determined patterns and determining the individual's state from the degree of similarity of the segments of the respiratory signal with said pre-determined patterns on the basis of certain pre-defined rules.

The patterns resulting from the involuntary contraction and relaxation of the diaphragm during respiration are governed by the sympathetic-vagal system and provide much information regarding individuals' physical and mental state, which, as discussed above, is reflected in their level of attention and reaction time. Advantageously, unlike in behaviour-based detection methods, wherein depending on the type of road the patterns that characterise a state can be concealed, the individuals' state of attention is always reflected in their way of breathing.

In a second embodiment, the method for determining an individual's state of attention comprises:

determining the time between successive crossings bearing the same slope sign of the respiratory signal with a threshold $T_h$ obtained from the individual's respiratory signal in a normal state, normalising said time between successive crossings by a time $T_{resp}$ corresponding to the average respiratory period of the individual's respiratory signal in a normal state, filtering to obtain a signal $K_s$, and filtering the absolute value of the derivative of signal $K_s$ normalised by the value $K_{sm}$ corresponding to the average absolute value of the derivative of signal $K_s$ in the stable respiratory interval, to obtain an index $dK_{snorm}$.

where threshold $T_h$ and the average respiratory period of the individual's respiratory signal in a normal state are obtained from the respiratory signal fragment selected to characterise the individual's normal state, or from the data stored in the memory device, in the event that no respiratory signal fragment is found that meets said pre-established criterion.

In a preferred embodiment, the level $T_h$ of the stable respiratory interval is determined as a percentile of the individual's respiratory signal in a normal state greater than 50%, preferably a percentile of approximately 70%.

In a preferred embodiment, the method for determining an individual's state of attention according to the second embodiment comprises determining the individual's state by comparing the normalised, filtered absolute value of the derivative of signal $K_s$ with at least one threshold and, optionally, taking into consideration the states of attention determined at previous times.

A second feature of this invention is that it provides a system designed to determine an individual's state of attention which comprises processing means adapted to implement the steps of the method according to any one of claims 1-21.

The system designed to determine an individual's state of attention according to the invention can be adapted to co-operate with a respiratory signal capture device or may itself comprise respiratory signal capture means, such as a plethysmography band, a pressure sensor, a piezoresistive sensor, a piezoelectric sensor, a micromechanical sensor, a microphone, an impedance sensor and a photoplethysmography sensor.

In an advantageous embodiment, the system designed to determine an individual's state of attention may comprise means of interaction with individuals, in order to inform them of an identified state of attention. Said means of interaction can be adapted to activate an alarm as a response to the detection of a pre-defined state of attention.

These and other aspects of the invention will become evident from, and clarified in reference to, the embodiments described further down in this document.

BRIEF DESCRIPTION OF THE FIGURES

In order to complement this description and contribute to a better understanding of the characteristics of the invention, according to an example of a preferred and practical embodiment thereof, a number of figures are included as an integral part of said description, which, for illustrative, non-limiting purposes, show the following.

Figures with the same reference numbers refer to the same elements.

DETAILED DESCRIPTION OF A PREFERRED EMBODIMENT

Below we describe an example of each of the two embodiments of the method for determining an individual's state of attention according to the present invention.

In the first embodiment, once the respiratory signal is obtained, it is segmented using, for example, a relevant peak algorithm such as the watershed algorithm, based on symbolic seeds, in order to simplify the respiratory signal and reduce the number of data which define it. A peak is considered to be relevant, and the seed thereof is validated, when it meets a set of requirements, such as: width, height and area greater than certain minimum values. In this way, the amount of information to be processed can be reduced by two orders of magnitude, from 2,000,000 data to 12,000 data. Once the respiratory signal is segmented, a representation thereof is obtained where each of the respiratory cycles can be independently observed.

In a first step of the method, the subject's normal respiratory characteristics are learnt and, in a second step, the respiratory signal is analysed in order to recognise pre-defined respiratory patterns and identify the subject's state.

In an example of preferred embodiment, a normal respiration fragment is selected by evaluating the amplitude and/or frequency of the respiratory signal in each respiratory signal fragment. Once a normal respiratory fragment is located, the following parameters are evaluated for each respiratory cycle:

Amplitude: evaluated as $(2 \cdot max - inf_i - inf_d)/2$. Three parameters will be evaluated: amplitude of one cycle, average amplitude of three cycles and average amplitude of five cycles. However, it might be that case that in other embodiments only one parameter would be evaluated, for example, the amplitude of one cycle.

Frequency (in number of cycles per minute): evaluated as: 60/time between two minima. Three parameters will be evaluated: frequency of one cycle, frequency of three cycles and frequency of five cycles.

Minimum value: the local minimum value of the respiratory cycle.

Maximum value: the local maximum value of the respiratory cycle.

Frequency symmetry: Max (rise time, fall time)/Min (rise time, fall time).

Amplitude symmetry: Max (max–$inf_i$, max–$inf_d$)/Min (max–$inf_i$, max–$inf_d$).

where $inf_i$ is the value corresponding to the left local minimum value of a respiratory cycle; $inf_d$ is the value corresponding to the right local minimum of a respiratory cycle; and max is the value corresponding to the local maximum of a respiratory cycle, said values being extracted from the respiratory signal fragment considered to be normal.

The normal respiratory cycle is characterised on the basis of the average value of the parameters evaluated for the entire normal respiratory fragment located.

It is understood that additional or alternative parameters and variables can be defined to characterise the individual's normal state.

For each segment of the respiratory signal, the same parameters that characterise the normal respiratory fragment are extracted. In the analysis step, once the method has been adapted to the individual's characteristics, the fuzzy parameters associated with each of the parameters evaluated are obtained. Subsequently, the degree of similarity of the segment analysed with respect to each of the previously defined patterns will be evaluated by means of a set of rules. The analysis step is implemented using fuzzy techniques in order to perform it in the same line wherein the technicians analyse the respiratory signal.

The advantage of using fuzzy logic in the first embodiment of the method of the invention is that it resolves the problem posed by the intraspecific variability which is involved in the analysis of a biomedical signal, since classification of the signal patterns is carried out on the basis of a loose pattern that allows for variability in the shape of the pre-defined patterns.

In this example of the first embodiment of the method of the invention, the parameters evaluated in each of the respiratory segments are classified on the basis of the following fuzzy parameters:

Minimum value: it is the local minimum value pertaining to the respiratory cycle. It is classified as high, normal, low, very low.

Maximum value: the local maximum value pertaining to the respiratory cycle. It is classified as high, normal, low, very low.

Amplitude: normal, low, very low.

Frequency: normal, low, very low.

Amplitude: symmetric, asymmetric, very asymmetric.

Frequency: symmetric, asymmetric, very asymmetric.

Within the context of the invention, classifying must be understood to mean assigning to each parameter a degree of belonging to each of at least two categories, as will be seen more clearly in the description of FIG. 1 below.

Figure 1:
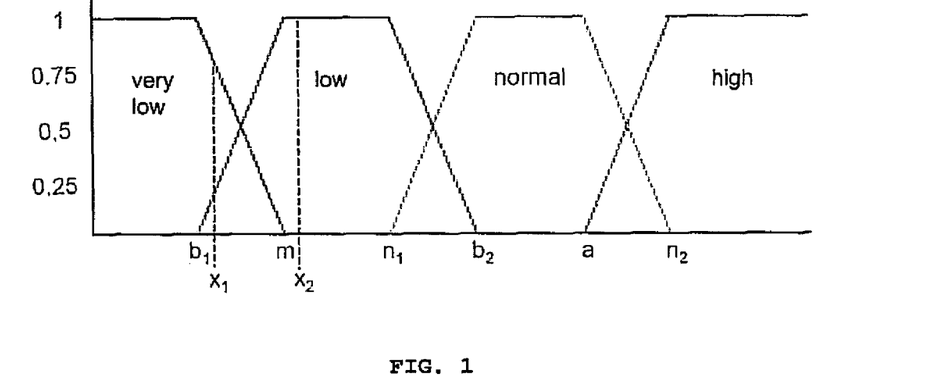
FIG. 1 shows the fuzzy values of the local minimum value and local maximum value pertaining to the respiratory cycle.
Figure 2:
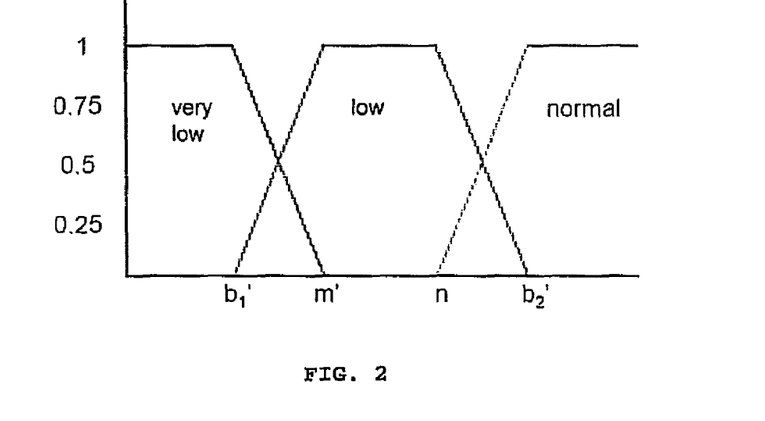
FIG. 2 shows the fuzzy values of amplitude, frequency, amplitude symmetry and frequency symmetry for the respiratory cycle.

FIGS. 1 and 2 show the above-mentioned fuzzy parameters: FIG. 1 for the minimum value and the maximum value, and FIG. 2 for amplitude, frequency, amplitude symmetry, and frequency symmetry. In both figures, the horizontal axis corresponds to one of the above-mentioned parameters (minimum value or maximum value in FIG. 1, and amplitude, frequency, amplitude symmetry or frequency symmetry in FIG. 2), normalised by the characteristic value of said parameter in the normal state, whereas the vertical axis, between 0 and 1, corresponds to the degree of belonging of said parameter to a category. In the case of FIG. 1, the categories are "very low", "low", "normal" and "high". In the case of FIG. 2, the categories are "very low", "low" and "normal".

As can be seen in said figures, in the method according to the first embodiment of this invention, a parameter does not necessarily have to be classified in a single category, but may be classified in two or more categories with a percentage of belonging to each of them. FIG. 1 shows an example of a first value $x_1$ of a parameter with a degree of belonging of approximately 0.8 to the "very low" category, a degree of belonging of approximately 0.2 to the "low" category and a degree of belonging of 0 to the "normal" and "high" categories. A second example in the same figure shows a second value $x_2$ of a parameter with a degree of belonging of 1 to the "low" category and a degree of belonging of 0 to the remaining categories.

The classification of the fuzzy parameters for the minimum value and the maximum value, as represented in FIG. 1, is the following:

| parameter value | degree of belonging | category |
|---|---|---|
| $x \leq b_1$ | 1 | very low |
| $b_1 < x < m$ | $(m - x)/(m - b_1)$ | very low |
|  | $(x - b_1)/(m - b_1)$ | low |
| $m \leq x \leq n_1$ | 1 | low |
| $n_1 < x < b_2$ | $(b_2 - x)/(b_2 - n_1)$ | low |
|  | $(x - n_1)/(b_2 - n_1)$ | normal |
| $b_2 \leq x \leq a$ | 1 | normal |
| $a < x < n_2$ | $(n_2 - x)/(n_2 - a)$ | normal |
|  | $(x - a)/(n_2 - a)$ | high |
| $n_2 \leq x$ | 1 | high |

In the above table, x represents the parameter (minimum value or maximum value), m is the point where the function that represents the "very low" category cuts the horizontal axis, $b_1$ and $b_2$ are the points where the function that represents the "low" category cuts the horizontal axis, where $b_1 < b_2$, $n_1$ and $n_2$ are the points where the functions that represent the "normal" category cut the horizontal axis, where $n_1 < n_2$, and a is the point where the function that represents the "high" category cuts the horizontal axis.

In a preferred embodiment of the invention, point m is approximately between 25% and 45%; point $b_1$ is approximately between 10% and 25%; point $b_2$ is approximately between 65% and 70%; point $n_1$ is approximately between 45% and 65%; point $n_2$ is approximately 100%; and point a is approximately between 80% and 90%. Within the context of this invention, the ends of the intervals will be understood to be included therein.

Similarly, the classification of the fuzzy parameters for the amplitude, frequency, amplitude symmetry and frequency symmetry, as represented in FIG. 2, is the following:

| parameter value | degree of belonging | category |
|---|---|---|
| $x \leq b_1'$ | 1 | very low |
| $b_1' < x < m'$ | $(m' - x)/(m' - b_1')$ | very low |
|  | $(x - b_1')/(m' - b_1')$ | low |
| $m' \leq x \leq n$ | 1 | low |
| $n < x < b_2'$ | $(b_2' - x)/(b_2' - n)$ | low |
|  | $(x - n)/(b_2' - n)$ | normal |
| $b_2' \leq x$ | 1 | normal |

In the above table, x represents the parameter (amplitude, frequency, amplitude symmetry or frequency symmetry), m is the point where the function that represents the "very low" category cuts the horizontal axis, $b_1'$ and $b_2'$ are the points where the function that represents the "low" category cut the horizontal axis, where $b_1'<b_2'$, and n is the point where the function that represents the "normal" category cuts the horizontal axis.

In a preferred embodiment of the invention, point m' is approximately between 50% and 60%; point $b_1'$ is approximately between 30% and 50%; point $b_2'$ is approximately between 85% and 93%, and point n is approximately between 75% and 90%.

Normal, low, and very low amplitude symmetry will be understood to correspond, respectively, to a symmetric, asymmetric and very asymmetric amplitude. The same applies to frequency symmetry.

Below we evaluate the degrees of similarity of each segment of the respiratory signal with previously determined respiratory phases. From the comparison of a respiratory signal with an EEG+EOG control signal, which objectively defines the driver's state of attention, several characteristic patterns for different respiratory phases have been defined.

Figure 3:
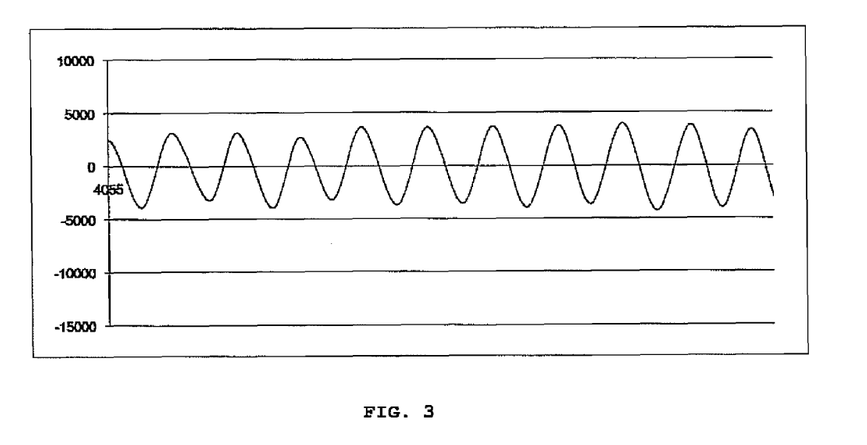
FIG. 3 shows a characteristic normal respiration pattern.

FIGS. 3-8 show some characteristic respiratory phase patterns corresponding to an example of the first embodiment of the method of the invention. Said respiratory phases are the following:

a) The normal respiration pattern is characterised by the rule;

A respiration segment constitutes normal respiration if the frequency is normal and symmetric, and the amplitude is normal and symmetric, and the maximum is normal and the minimum is normal.

Figure 4:
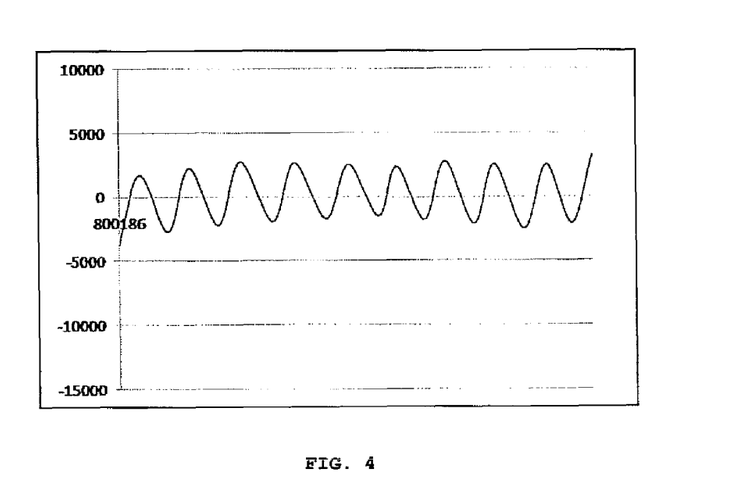
FIG. 4 shows a characteristic low-amplitude relaxation respiration pattern.
Figure 5:
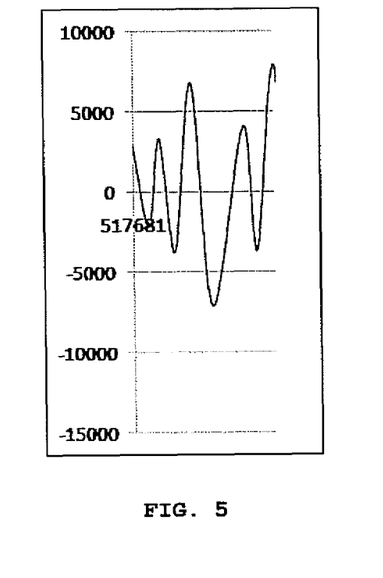
FIG. 5 shows a characteristic relaxation-sigh pattern.
Figure 6:
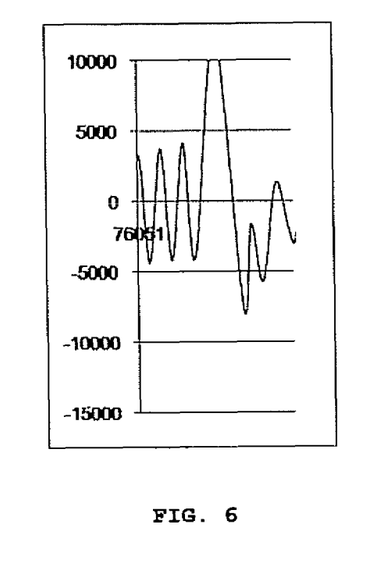
FIG. 6 shows a characteristic fatigue-sigh pattern.
Figure 7:
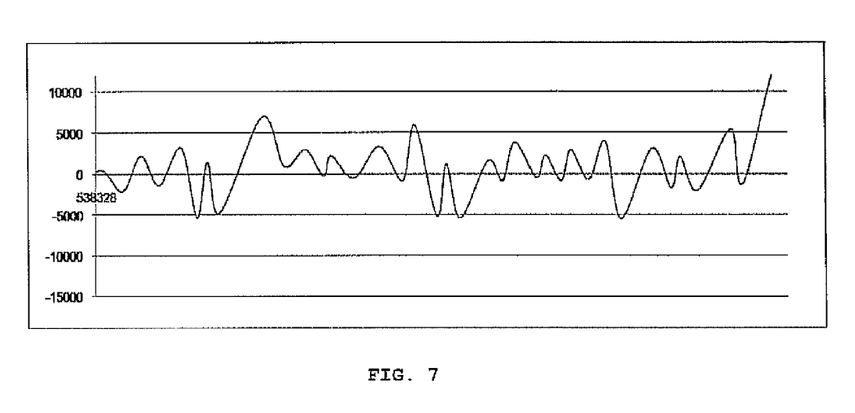
FIG. 7 shows a characteristic chaotic-phase pattern.
Figure 8:
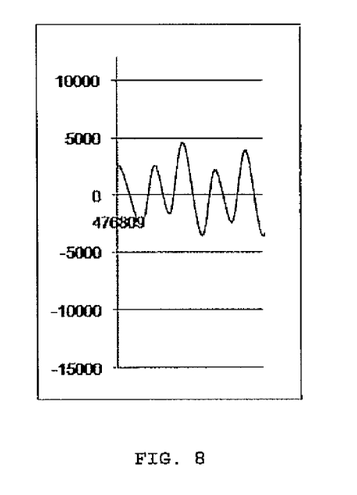
FIG. 8 shows a characteristic M pattern.

For example, a respiratory fragment that includes at least 20 respiratory cycles can be considered to constitute normal respiration if all the minima are sufficiently homogeneous, and all the maxima are sufficiently homogeneous, and all the frequencies are sufficiently homogeneous and symmetric, and all the amplitudes are sufficiently symmetric.

b) The low-amplitude relaxation respiration pattern is characterised by the rule:

A respiration segment constitutes low-amplitude relaxation respiration if: the frequency is normal and symmetric, and the amplitude is low and symmetric, and the maximum is normal or low, and the minimum is normal; or if
the frequency is normal and symmetric, and the amplitude is low and symmetric, and the maximum is normal and the minimum is normal or high.

c) The low-frequency relaxation respiration pattern is characterised by the rule:

A respiration segment constitutes low-frequency relaxation respiration if: the frequency is low and symmetric, and the amplitude is normal and symmetric, and the maximum is normal or low, and the minimum is normal; or if
the frequency is low and symmetric, and the amplitude is normal and symmetric, and the maximum is normal and the minimum is normal or high.

d) The relaxation sigh pattern is characterised by the rule:
A respiration segment constitutes a relaxation sigh if the frequency is low, and the maximum is high or very high, and the minimum is low or very low.

e) The fatigue sigh pattern is characterised by the rule:
A respiration segment constitutes a fatigue sigh if the frequency is low or very low, and the amplitude is very high, and the amplitude is asymmetric or very asymmetric, and the maximum is very high and the minimum is very low.

f) Chaotic respiration, characterised by the rule:

A respiration segment has a chaotic pattern if the frequency is low or very low, and the frequency is asymmetric or very asymmetric, and the amplitude is low or very low, and the amplitude is asymmetric or very asymmetric, and the maximum is normal or high, and the minimum is normal or low.

g) The M pattern is characterised by the rule:
A respiration fragment that includes three consecutive minima has an M pattern if the left minimum is normal, and the central minimum is high or very high, and the right minimum is normal, and the left maximum is low or normal, and the right maximum is low or normal.

Other respiratory phases with additional or alternative characteristic patterns can be defined. Furthermore, respiratory patterns can be associated with phases wherein the individual is, for example, singing, coughing, talking or performing other actions.

By evaluating the degree of similarity of each segment of the respiratory signal to each of the pre-defined patterns, it is possible to identify which pre-defined respiratory patterns should be associated with each segment of respiratory signal. Thus, the method interprets an individual's respiratory signal as a succession of pre-defined patterns, wherefrom it can determine the individual's state of attention. In a preferred embodiment, a percentage of similarity and a confidence index are determined, and, for each segment, the pattern with the greatest similarity and the highest confidence is selected.

Finally, on the basis of the respiratory phases determined to be associated with each segment of the respiratory signal and certain pre-defined rules, the individual's state of attention is determined. The state of attention can be determined by classifying the individual's actual state into one of at least two pre-defined states. As an alternative, the state of attention can be determined by assigning a degree of belonging to one or more states of attention.

In a particular example of the detection of a state of drowsiness, the method of the invention according to the first embodiment makes it possible to evaluate an individual's degree of attention in one or several states corresponding to: wakefulness, fatigue, drowsiness and deep drowsiness, on the basis of pre-defined rules:

A state is considered to be a wakefulness state when almost all cycles are normal respiration cycles, there can be some relaxation sighs with their short accommodation period, or some short relaxation respiration cycle. A state will also be considered to be a wakefulness state when the individual is talking or singing/humming.

A state is considered to be a fatigue state when almost all cycles are relaxation respiration cycles and there is a large number of relaxation sighs with their short accommodation period. Some fatigue sighs may occur.

A state is considered to be a drowsiness state when there are many chaotic cycles as well as a large number of relaxation and fatigue sighs. Short accomodation cycles may occur.

A state is considered to be a state of deep drowsiness when there are only chaotic cycles, and cycles of relaxation and fatigue sighs.

Figure 9:
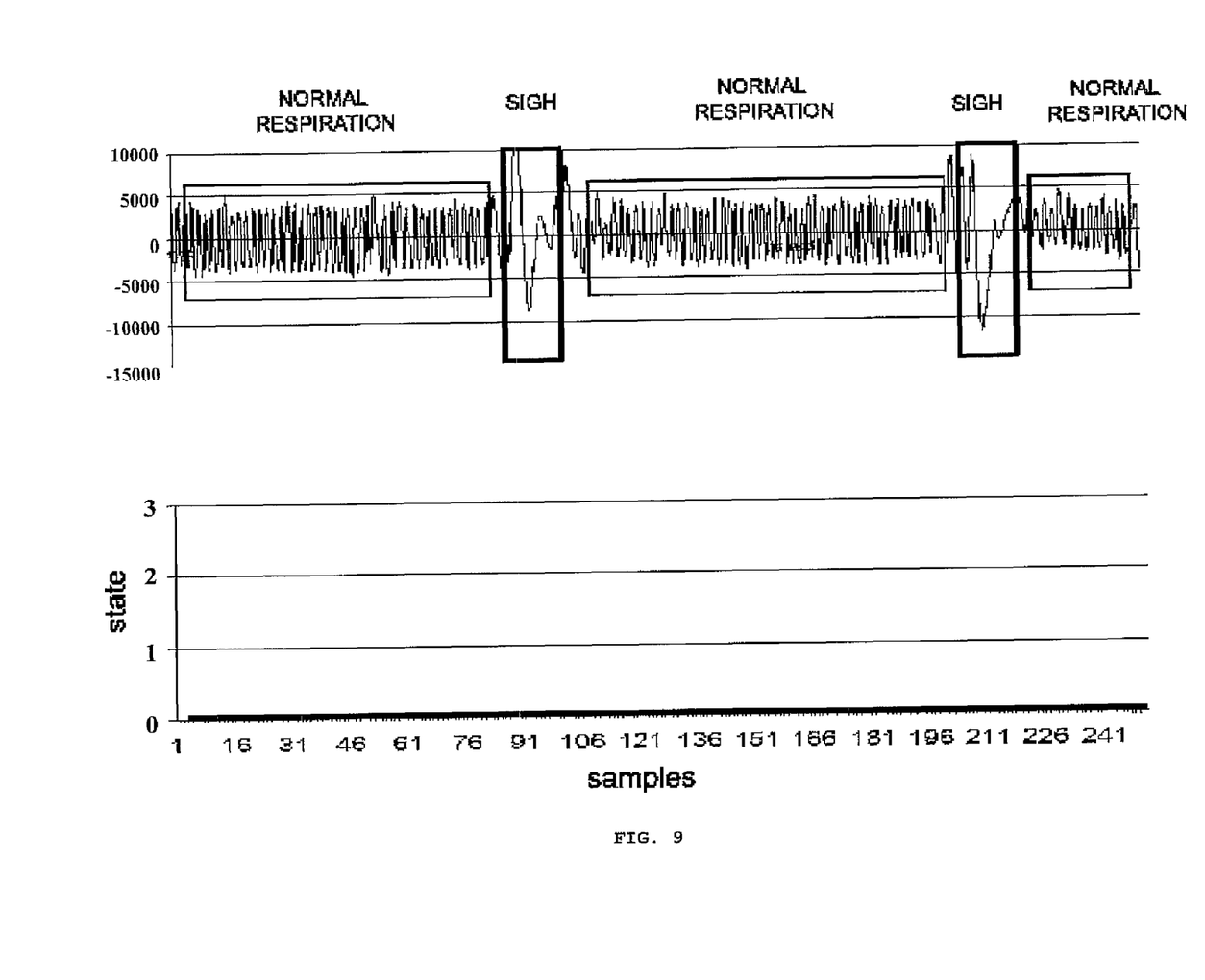
FIG. 9 shows a first example of the method of the invention according to a first embodiment for a drowsiness detection application.

FIG. 9 shows an example of the method for determining an individual's state of attention according to the first embodiment, in an application designed to determine the individual's degree of drowsiness. The upper part of the figure shows the time evolution of an individual's respiratory signal in arbitrary units. Several segments of respiratory signal have been identified as pre-defined patterns by means of the method of the invention, and are marked with rectangles. It can be seen that, as discussed above, a segment of respiratory signal may contain a respiratory cycle, or multiples or submultiples of a cycle.

As the figure shows, the entire signal represented corresponds to a state of normal respiration with fragments pertaining to sighs inserted therein. This is why the method of the invention identifies the signal as a succession of patterns of normal respiration and sighs.

The lower part of the figure shows, on the vertical axis, an index that is representative of the individual's state of attention, value 0 pertaining to a normal state or state of wakefulness, value 1 to a state of fatigue, value 2 to a state of drowsiness and value 3 to a state of deep drowsiness, whereas the horizontal axis shows the sample number of the respiratory signal represented in the upper part of the figure sampled. It can be observed that the method has determined that the individual is in state 0, i.e. in a state of wakefulness, throughout the analysis, since most of the respiratory cycles correspond to the normal state and some sighs appear.

Figure 10:
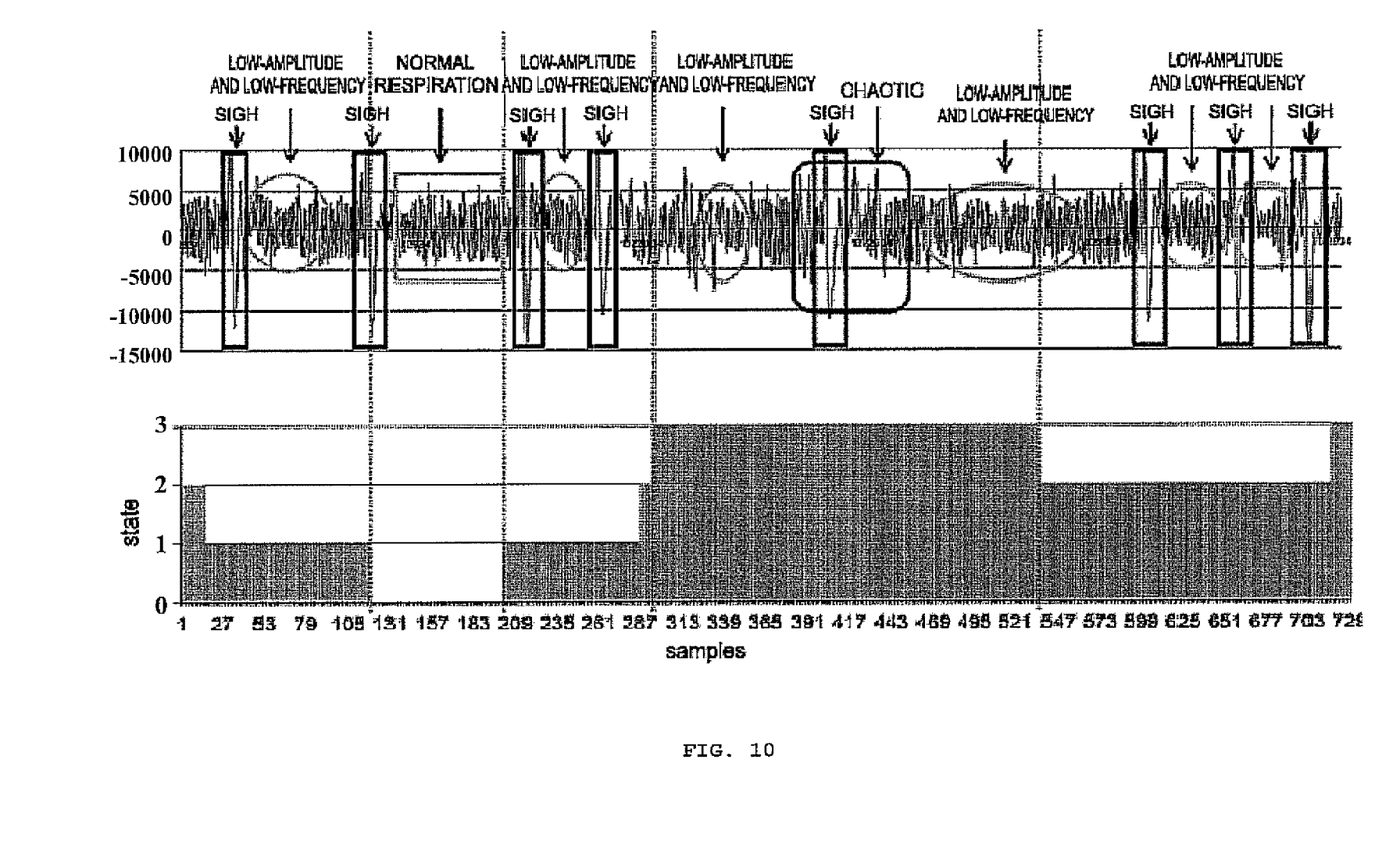
FIG. 10 shows a second example of the method of the invention according to a first embodiment for a drowsiness detection application.

FIG. 10 shows a second example of the first embodiment of the method of the invention. As in FIG. 9, the upper part of the figure shows the time evolution of an individual's respiratory signal and the lower part shows the state determined by the method as a function of the sample number of the sampled signal. There are two areas wherein the method of the invention has identified low-amplitude and/or low-frequency patterns (marked as ellipses), and patterns of high-frequency sighs (marked as rectangles), This sequence of patterns corresponds to a state of fatigue, labelled as state 1 in the figure. Between the two areas identified as states of fatigue there is an area with a normal respiration pattern (marked as a rectangle), corresponding to an interval during which the individual has recovered the state of wakefulness, labelled as state 0.

The last part of the respiratory signal exhibits an increase in the frequency of sighs, jointly with low-amplitude and/or low-frequency patterns, which, according to pre-established rules, is indicative of a state of drowsiness, labelled as state 2. Finally, chaotic patterns (marked as rectangles with rounded corners), in addition to low-amplitude and/or low-frequency patterns, appear in the central part of the signal, which is identified as a state of deep drowsiness, labelled as state 3. This figure clearly shows the correlation between the type of patterns identifiable in the respiratory signal and the degree of attention determined.

The method according to the first embodiment has the advantage of detecting variations in the respiratory signal that are characteristic of different states of attention. It does so by analysing the respiratory signal with a pattern-based fuzzy method that makes the method for determining the state of attention more robust, since it increases the specificity and the sensitivity thereof, and prevents the effect that variability between individuals has on existing methods that are based on the analysis of biomedical data.

Below the method of the invention according to a second embodiment will be described. This second embodiment is based on the fact that, during the transition between a normal state of attention and the onset of sleep, ventilation becomes unstable. Similarly, it is possible to characterise the transition between a normal state of attention and an anomalous state where the subject is under the influence of stress, drugs, alcohol or other factors. Thus, although in this example the second embodiment will be described as applied to a case of detection of drowsiness, it should not be considered to be limited to said application.

During drowsiness, the expiratory phase increases, as do the pauses between successive respirations. Once the subject is asleep, respiration returns to values similar to those of an alert state. Thus, variations in the respiratory signal are analysed and an index is defined which represents these variations per unit of time. By establishing suitable thresholds for the states to be detected, for example, for fatigue and for drowsiness, the patient's state can be classified into wakefulness, fatigue and drowsiness depending on the values of the calculated index.

To this end, an individual's respiratory signal is obtained, for example, by means of a plethysmographic band placed on the abdomen at the height of the diaphragm, and a signal fragment corresponding to an individual's normal state is selected according to a pre-established criterion. Said normal respiration fragment can be located within an interval of pre-determined duration that begins when measurement of the signal starts. For example, a stable respiratory interval lasting 40 seconds can be sought during the first 3 minutes of signal acquisition, although the duration of the interval and the total search time may be different. On the other hand, the normal respiration fragment can also be selected at any time during the process of determining the individual's state of attention, and it is possible to update the state characterised as normal if a second respiratory signal fragment meets the pre-established criterion better than a first, previously selected respiratory signal fragment.

In the event that no respiratory signal fragment is found that meets said pre-established criterion, the method of the invention specifies that the individual's normal state can be characterised on the basis of data stored in a memory device, as previously discussed.

In a preferred embodiment, the stable respiratory interval is selected as the window that minimises a heteroscedasticity statistical variable, $RCX_{Wi}$, which is representative of the variability of the respiratory signal. To this end, said statistical variable is calculated for a series of respiratory signal fragments and the window for which the statistical variable reaches the minimum value is determined.

In an embodiment example, the search for the stable respiratory interval is performed on the individual's respiratory signal previously sampled at a given frequency, for example, 250 Hz, with a sliding window with a delay of a sample between successive windows. In the case of the sampled signal, a possible expression for said heteroscedasticity statistical variable is given by:

$$RCX_{Wi} = \frac{1}{M} \sum_{n=1}^{M} \left| \left[ \frac{\sum_{i=1}^{n}(Resp(i))^2}{\sum_{i=1}^{M}(Resp(i))^2} \right] - \frac{n}{M} \right|$$

where Resp(i) is the i-th respiratory sample within the window with M samples.

Once the normal respiratory fragment is recognised, defined by an initial instant, $T_{ini}$, and a final instant, $T_{fin}$, it is characterised as a normal state in order to subsequently perform comparisons and normalisations. To this end, a threshold $T_h$ and an average respiratory period, $T_{resp}$ are extracted from said normal respiration signal fragment. Threshold $T_h$ corresponds in an advantageous embodiment to a percentile of the respiratory signal greater than 50% and, preferably, of approximately 70%.

Once the normal state is characterised, the instants when the measured respiratory signal crosses threshold $T_h$ with a given slope sign are detected and the time between successive crossings of said threshold is calculated, and normalised by the average respiratory period of the normal respiratory fragment, $T_{resp}$. Subsequently, a filtering is performed to obtain a signal $K_s$. Any filtering method can be used, such as a moving-average filter with a duration of N respiratory cycles, for example, 4 respiratory cycles. Normalisation is performed in order to correct for the fact that different subjects breathe at different frequencies.

The final index is obtained by calculating the absolute value of the derivative of signal $K_s$, normalised by the value $K_{sm}$, corresponding to the average absolute value of signal $K_s$ in the stable respiratory interval, which makes it possible to correct for the fact that some subjects have a more or less stable respiration, and filtering the result. A moving-average filter can be used with a duration of N' respiratory cycles, for example, 10 cycles, although other filters are equally adequate. The signal obtained is called $dK_{snorm}$.

Finally, in a preferred embodiment, the individual's state of attention is determined by comparing the value obtained in the previous step with at least one threshold that establishes the separation between different states of attention, for example, between a normal state and a state of fatigue or between a state of fatigue and a state of drowsiness.

In addition to the comparison with said threshold values, a correlation with states determined at previous times may be considered. For example, given a scale of states 0-1-2-3, where state 0 corresponds to the state of normal attention and state 3 corresponds to the state of lowest attention, the method may consider that a state determined to be a state of attention 3 immediately following a state determined to be a state of attention 0 corresponds to an artefact of the respiratory signal, unless the following state determined is once again a state of attention 3. In this way, by defining a number of correlation rules, it is possible to make the criterion used to determine the individual's state of attention more flexible, in addition to reducing the number of false non-attention alerts.

Figure 11:
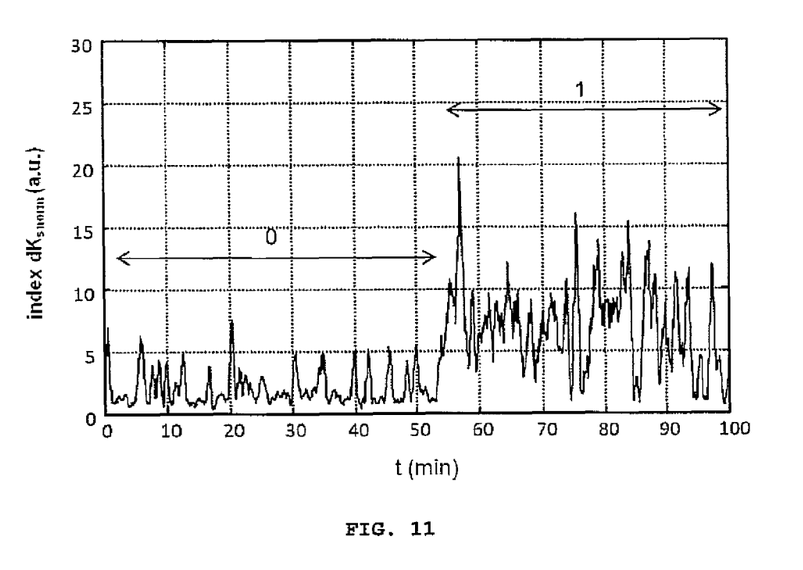
FIG. 11 shows an example of the method of the invention according to a second embodiment for a drowsiness detection application.

FIG. 11 shows an example of a result of the method for determining a state of attention according to the second embodiment. Said graph represents index $dK_{snorm}$ against time and a first state of attention, classified as "state 0" and corresponding to a normal state, a state of wakefulness, may be observed, followed by a transition, approximately at minute 53, to a second state of attention, classified as "state 1" and pertaining to a state of fatigue and/or drowsiness. For this specific example, a threshold value of 6 was used, although it is understood that index $dK_{snorm}$ may have another value for other embodiments.

The invention claimed is:

1. A method for determining an individual's state of attention, which comprises the following operational steps:
   a) providing a respiratory signal capture apparatus,
   b) obtaining an individual's respiratory signal with the respiratory signal capture apparatus,
   c) segmenting said respiratory signal into a plurality of segments,
   d) extracting at least one parameter from each segment of the respiratory signal,
   e) characterising a normal state of attention for the individual by selecting a respiratory signal fragment that is considered to be normal according to a pre-established criterion and, in the event that no respiratory signal fragment is found that meets said pre-established criterion, characterising the normal state of attention for the individual on the basis of certain data stored in a memory device, and
   f) determining the individual's state of attention from the at least one parameter extracted from each segment on the basis of pre-defined rules and the normal state of attention for the individual, wherein step d) comprises obtaining at least one fuzzy parameter from the at least one parameter extracted from each segment, and step f) comprises: evaluating a degree of similarity of each segment with respect to each one of a plurality of pre-determined phases, by comparing the at least one fuzzy parameter of each segment to characteristic parameters for said pre-determined phases, and determining the individual's state of attention from the degree of similarity of the segments of the signal with respect to said pre-determined phases on the basis of certain pre-defined rules.

2. The method for determining an individual's state of attention, according to claim 1, characterised in that said certain data stored in the memory device are data pertaining to the subject him/herself and/or data for a set of subjects that statistically represent a population.

3. The method for determining an individual's state of attention, according to claim 1, characterised in that step e) comprises: determining the variability of the respiratory signal in the signal fragment considered, or evaluating the degree of similarity of the respiratory signal fragment considered with respect to a model respiratory signal pattern, or evaluating the homogeneity of certain given variables in the respiratory cycles within the respiratory signal fragment in question.

4. The method for determining an individual's state of attention, according to claim 1, characterised in that the at least one parameter is selected from the group constituted by amplitude, frequency, minimum value, maximum value, amplitude symmetry and frequency symmetry.

5. The method for determining an individual's state of attention, according to claim 1, characterised in that step c), wherein the respiratory signal is segmented, comprises using a watershed relevant peak algorithm in order to reduce the amount of information to be processed.

6. The method for determining an individual's state of attention, according to claim 1, characterised in that at least one of the pre-determined phases is selected from the group constituted by normal respiration, low-amplitude relaxation respiration, low-frequency relaxation respiration, relaxation sigh, fatigue sigh, chaotic phase, yawning, talking, singing/humming and M pattern.

7. The method for determining an individual's state of attention, according to claim 6, characterised in that the "normal respiration" phase corresponds to a normal, symmetric frequency, a normal, symmetric amplitude, a normal maximum value and a normal minimum value.

8. The method for determining an individual's state of attention, according to claim 6, characterised in that the "low-amplitude relaxation respiration" phase corresponds to a normal, symmetric frequency, a low, symmetric amplitude, a normal or low maximum and a normal minimum, or a normal, symmetric frequency, a low, symmetric amplitude, a normal maximum, and a normal or high minimum.

9. The method for determining an individual's state of attention, according to claim 6, characterised in that the "low-frequency relaxation respiration" phase corresponds to a low, symmetric frequency, a normal, symmetric amplitude, a normal or low maximum and a normal minimum, or a low, symmetric frequency, a normal, symmetric amplitude, a normal maximum, and a normal or high minimum.

10. The method for determining an individual's state of attention, according to claim 6, characterised in that the "relaxation sigh" phase corresponds to a low frequency, a high or very high maximum, and a low or very low minimum.

11. The method for determining an individual's state of attention, according to claim 6, characterised in that the "fatigue sigh" phase corresponds to a low or very low frequency, a very high, asymmetric or very asymmetric amplitude, a very high maximum, and a very low minimum.

12. The method for determining an individual's state of attention, according to claim 6, characterised in that the "chaotic respiration" phase corresponds to a low or very low, asymmetric or very asymmetric frequency, a low or very low, asymmetric or very asymmetric amplitude, a normal or high maximum, and a normal or low minimum.

13. The method for determining an individual's state of attention, according to claim 6, characterised in that the "M pattern" phase corresponds to a signal fragment with three consecutive minima that exhibit the following characteristics: the left minimum is normal, the central minimum is high or very high, the right minimum is normal, the left maximum is low or normal, and the right maximum is low or normal.

14. The method for determining an individual's state of attention, according to claim 1, characterised in that the determination of the individual's state of attention comprises supplementing the analysis of the respiratory signal with data obtained from a second source.

15. The method for determining an individual's state of attention, according to claim 1, characterised in that it comprises informing the individual of the state of attention determined.

16. The method for determining an individual's state of attention, according to claim 15, characterised in that it comprises activating an alarm in response to the detection of a given state of attention.

17. A method for determining an individual's state of attention, which comprises the following operational steps:
    a) providing a respiratory signal capture apparatus,
    b) obtaining an individual's respiratory signal with the respiratory signal capture apparatus,
    c) segmenting said respiratory signal into a plurality of segments,
    d) extracting at least one parameter from each segment of the respiratory signal,
    e) characterising a normal state of attention for the individual by selecting a respiratory signal fragment that is considered to be normal according to a pre-established criterion and, in the event that no respiratory signal fragment is found that meets said pre-established criterion, characterising the normal state of attention for the individual on the basis of certain data stored in a memory device, and
    f) determining the individual's state of attention from the at least one parameter extracted from each segment on the basis of pre-defined rules and the normal state of attention for the individual, characterised in that: step f) comprises: determining the time between successive crossings with the same slope sign of the respiratory signal with a threshold $T_h$ obtained from the individual's respiratory signal in a normal state of attention, normalising said time between successive crossings by a time $T_{resp}$ corresponding to the average respiratory period of the individual's respiratory signal in a normal state of attention, filtering to obtain a signal $K_s$, and filtering the absolute value of the derivative of signal $K_s$, normalised by the value corresponding to the average absolute value of the derivative of signal $K_s$ in the stable respiratory interval, where threshold $T_h$ and the average respiratory period of the individual's respiratory signal in a normal state of attention are obtained from the respiratory signal fragment selected to characterise the individual's normal state of attention, or from the data stored in the memory device, in the event that no respiratory signal fragment is found that meets said pre-established criterion.

18. The method for determining an individual's state of attention, according to claim 17, characterised in that step f) comprises determining the individual's state of attention by comparing the normalised, filtered absolute value of the derivative of signal $K_s$ to at least one threshold, and, optionally, taking into consideration the states of attention determined at previous times.

19. The method for determining an individual's state of attention, according to claim 17, characterised in that level $T_h$ of the stable respiratory interval is determined as a percentile of the individual's respiratory signal in a normal state of attention greater than 50%.

20. The method for determining an individual's state of attention, according to claim 17, characterised in that the determination of the individual's respiratory signal in a normal state of attention comprises: calculating a statistical variable $RCX_{Wi}$ for different respiratory signal fragments, and selecting the fragment with the most stable variance, which minimises statistical variable $RCX_{Wi}$.

21. The method for determining an individual's state of attention, according to claim 20, characterised in that statistical variable $RCX_{Wi}$ is obtained from a heteroscedasticity test.

22. The method for determining an individual's state of attention, according to claim 21, characterised in that statistical variable $RCX_{Wi}$ is:

$$RCX_{Wi} = \frac{1}{M} \sum_{n=1}^{M} \left| \left[ \frac{\sum_{i=1}^{n} (Resp(i))^2}{\sum_{i=1}^{M} (Resp(i))^2} \right] - \frac{n}{M} \right|$$

where Resp(i) is the i-th respiratory sample within a window with M samples of the sampled respiratory signal.

23. A system for determining an individual's state of attention, the system comprising:
    a respiratory signal capture apparatus; and
    a processor for performing the following:
    a) receiving an individual's respiratory signal from the respiratory signal capture apparatus,
    b) segmenting said respiratory signal into a plurality of segments,
    c) extracting at least one parameter from each segment of the respiratory signal,
    d) characterising a normal state of attention for the individual by selecting a respiratory signal fragment that is considered to be normal according to a pre-established criterion and, in the event that no respiratory signal fragment is found that meets said pre-established criterion, characterising the normal state of attention for the individual on the basis of certain data stored in a memory device, and
    e) determining the individual's state of attention from the at least one parameter extracted from each segment on the basis of pre-defined rules and the normal state of attention for the individual,
    wherein step c) comprises obtaining at least one fuzzy parameter from the at least one parameter extracted from each segment, and step e) comprises: evaluating the degree of similarity of each segment with respect to each one of a plurality of pre-determined phases, by comparing the at least one fuzzy parameter of each segment to characteristic parameters for said pre-determined phases, and determining the individual's state of attention from the degree of similarity of the segments of the signal with respect to said pre-determined phases on the basis of certain pre-defined rules.

24. The system for determining an individual's state of attention, according to claim 23, which comprises means for capturing a respiratory signal.

25. The system for determining an individual's state of attention, according to claim 23, which comprises means for interacting with the individual, in order to inform them of a given state of attention.

26. The system for determining an individual's state of attention, according to claim 25, wherein the means for interacting with the individual are adapted for activating an alarm in response to the detection of a state of attention.

27. A vehicle that comprises the system, according to claim 23.

28. A computer readable medium having program code means embodied therein for determining an individual's state of attention, the program code means comprising:
 a) obtaining an individual's respiratory signal from a respiratory signal capture apparatus,
 b) segmenting said respiratory signal into a plurality of segments,
 c) extracting at least one parameter from each segment of the respiratory signal,
 d) characterising a normal state of attention for the individual by selecting a respiratory signal fragment that is considered to be normal according to a pre-established criterion and, in the event that no respiratory signal fragment is found that meets said pre-established criterion, characterising the normal state of attention for the individual on the basis of certain data stored in a memory device, and
 e) determining the individual's state of attention from the at least one parameter extracted from each segment on the basis of pre-defined rules and the normal state of attention for the individual, wherein step c) comprises obtaining at least one fuzzy parameter from the at least one parameter extracted from each segment, and step e) comprises: evaluating a degree of similarity of each segment with respect to each one of a plurality of pre-determined phases, by comparing the at least one fuzzy parameter of each segment to characteristic parameters for said pre-determined phases, and determining the individual's state of attention from the degree of similarity of the segments of the signal with respect to said pre-determined phases on the basis of certain pre-defined rules.

* * * * *